United States Patent [19]

Demel

[11] Patent Number: 5,718,334
[45] Date of Patent: Feb. 17, 1998

[54] CONTAINER CLOSURE FOR FLEXIBLE CONTAINERS

[75] Inventor: Robert J. Demel, Coto de Coza, Calif.

[73] Assignee: Allergan, Waco, Tex.

[21] Appl. No.: 712,189

[22] Filed: Sep. 11, 1996

[51] Int. Cl.⁶ .................................................. A61B 17/06
[52] U.S. Cl. .................. 206/438; 206/364; 206/222; 215/12.1; 215/344
[58] Field of Search ........................ 206/438, 363, 206/364, 367, 222; 220/404, 410, 254; 215/12.1, 12.2, 307, 310, 320, 321, 344, 354

[56] References Cited

U.S. PATENT DOCUMENTS

| | | | |
|---|---|---|---|
| 3,476,277 | 11/1969 | Rownd | 215/12.1 |
| 4,239,132 | 12/1980 | Mueller et al. | |
| 4,330,066 | 5/1982 | Berliner | 215/12.1 |
| 4,469,250 | 9/1984 | Evezich | |
| 4,595,434 | 6/1986 | Eckstein et al. | |
| 4,760,937 | 8/1988 | Evezich | |
| 4,909,416 | 3/1990 | Evezich | |
| 5,230,428 | 7/1993 | McShane | 206/364 |
| 5,305,920 | 4/1994 | Reiboldt et al. | |
| 5,312,018 | 5/1994 | Evezich | |
| 5,397,026 | 3/1995 | Mayes | |
| 5,421,470 | 6/1995 | Dudzik | 215/343 |

*Primary Examiner*—Paul T. Sewell
*Assistant Examiner*—Nhan T. Lam
*Attorney, Agent, or Firm*—Walter A. Hackler

[57] ABSTRACT

Container closure apparatus includes a rigid container having an open end with a top edge along with a a collapsible container disposed within the rigid container and having an open end. A cap is provided for covering the rigid and flexible container open ends and a plug seal provides a primary seal between the rigid container and the flexible container. The plug seal includes, in combination, a peripheral outwardly extending wall portion on the flexible container and a depending portion, extending from the cap, for pressing the wall portion against an inside wall of the rigid container. A gasket seal provides a secondary seal between the rigid container and the flexible container. The gasket seal includes, in combination, a lip outwardly extending from the flexible container open end and a groove, disposed in the cap, for pressing the lip against the rigid container top edge. The cap is secured to the rigid container in a position enabling the depending portion means to press the extending wall against the rigid container inside wall and enabling the groove to press lip against the rigid container top edge.

17 Claims, 2 Drawing Sheets

CONTAINER CLOSURE FOR FLEXIBLE CONTAINERS

The present invention is generally directed to apparatus for administering preservative-free formulations of medicament such as eye drop containers.

More particularly, the present invention is directed to the sealing of packaging which includes a rigid container having a flexible bag or pouch for containing a container for a dropwise dispenser.

A wide variety of packages are known which include an outer rigid bottle and inner flexible or collapsible product bag or pouch. The inner product bag collapses as the product is dispensed.

It is obvious that such inner pouches or bags must be formed from materials having little or no interaction with the intended contents thereof in order to prevent contamination of the contained fluids. The selection of container materials is particularly important for drug/pharmaceutical products since changes in a particular drug formulation due to impurities introduced by or through the container wall, and changes in drug formulation over time due to migration of various components through the container walls can have a profound effect on the product performance in both physical and chemical terms.

This problem is acute for flexible or pliable containers or pouches. Many materials suitable for the construction of collapsible bags or pouches such as polyethylene, Kraton, C-Flex, Sarlink and the like are not suitable due to the adsorption or permeation of drug formulations or preservatives therethrough.

Upon selection of a suitable material or combination of materials such as, for example, said forth in U.S. patent application Ser. No. 08/536,202 filed Sep. 29, 1995, a problem still exists in methods in apparatus for sealing the formulation within the flexible pouch and at the same time sealing the flexible pouch to the rigid outer container which facilitates handling and dispensing of the formulation from the flexible pouch bag disposed therein.

Accordingly, the present invention is specifically directed to a container closure for such devices.

SUMMARY OF THE INVENTION

A container closure apparatus in accordance with the present invention generally includes a rigid container having an open end with a top edge along with a collapsible container disposed therein having an open end.

The cap provides a means for covering the rigid and flexible container open ends. A plug seal provides a means for providing a primary seal between the rigid container and the flexible container with the plug seal means comprising in combination a peripheral outwardly extending wall portion on the flexible container and a depending portion extending from the cap which provides a means for pressing the wall portion against the inside wall of the rigid container.

A further gasket seal means provides a secondary seal between the rigid container and the flexible container with the gasket seal means comprising in combination a lip outwardly extending from the flexible container open end and a groove disposed in the cap, which provides means for pressing the lip against the rigid container top or edge.

Means are provided for securing the cap to the rigid container in a position enabling depending portion to press the extending wall of the flexible container against the rigid container inside wall and further enabling the groove means to press the lip against the rigid container top edge.

Importantly, means are provided for preventing slippage of the lip from the groove. This is particularly important in assembly of the container closure apparatus in which the cap means is moved into a position pressing the extending wall portion of the flexible container against a rigid container. During this procedure, slippage of the lip groove and from proper position against the top edge of the rigid container is prevented by a pointed raised ridge disposed on a bottom of the groove in combination with a pointed raised ridge disposed on the rigid container top edge.

Preferably, these pointed ridges are aligned with one another to prevent movement of the lip during and after assembly of the container closure apparatus with the cap covering the rigid and the flexible container open ends.

More particularly, the container closure apparatus in accordance with the present invention includes a flexible container with a length greater than the length of the original container and means are provided which define a narrow region in the flexible container for enabling inward folding of a flexible container wall when the cap means is secured to the rigid container. In this manner controlled reliable folding of the flexible container within the rigid container is accomplished.

The extending wall portion of the flexible container is congruent with the lip and the narrow region in the flexible container hereinabove described is disposed adjacent thereto which also prevents a remainder of the flexible container from interfering with the plug seal established between the rigid container and the flexible container.

More particularly, the depending portion of the cap extends from the bottom of the groove to a point along the flexible container past the extending wall portion.

The means for securing the caps means to the rigid container may include a skirt, sized for placement over the rigid container open end, having means for engaging the rigid container. Further, the rigid container may include protruding latch members and the means for engaging the rigid container may include recessed portions positioned to engage the latch members.

In addition, the cap may include means which define and indicate a thin portion thereof, for facilitating needle puncture in order to fill the flexible container with a liquid without puncture of the folded flexible container wall.

BRIEF DESCRIPTION OF THE DRAWINGS

The present invention can be more readily understood by consideration of the following detailed description, particularly in conjunction with the accompanying drawings in which.

DETAILED DESCRIPTION

Figure 1:
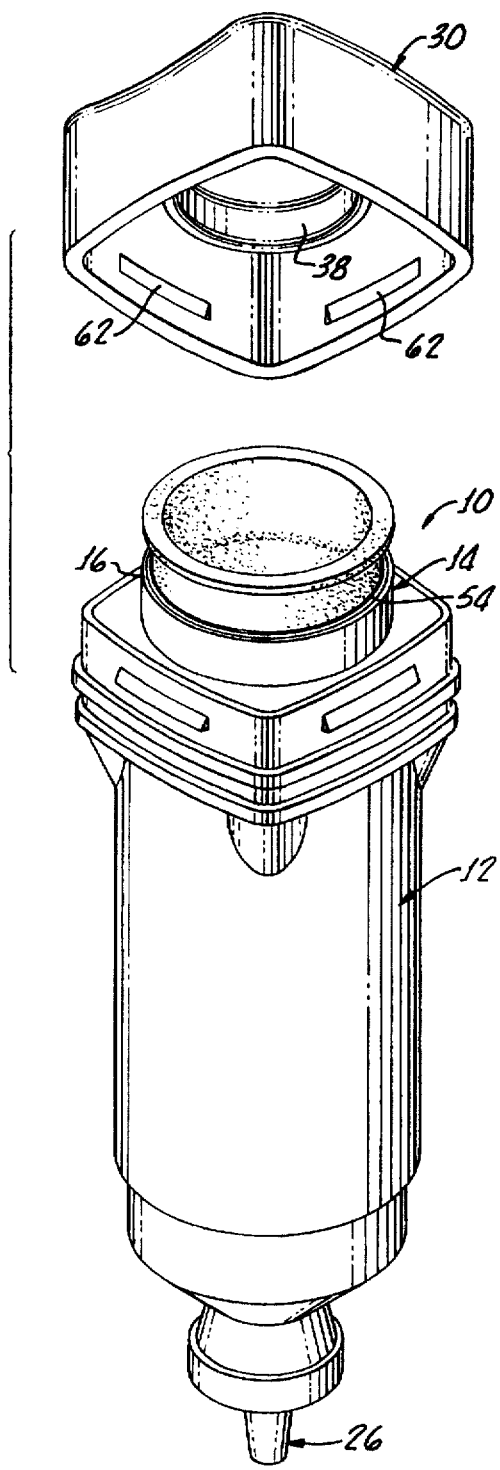
FIG. 1 is a perspective view of a container closure apparatus in accordance with the present invention showing a flexible container or pouch disposed within a rigid container along with a cap for covering the containers.

Turning now to FIG. 1 there is shown a container closure apparatus 10 which generally includes a rigid container 12 having an open end 14 with an exposed top edge 16 thereon. The rigid container may be formed from any suitable rigid material such as, for example, ABS (Acrylonitrile-Butadiene-Styrene) or pylycarbonate.

A flexible container, or pouch, 20 disposed within the rigid container 12 provides a means for containing a liquid, not shown. The flexible container 20 may be formed of any suitable thermo plastic elastomer such as, for example, Kraton® rubber. The flexible container or pouch 20 includes a collapsible side wall 22 for enabling the dispensement of the liquid contained therein through a nozzle 26 without entry of ambient air thereinto. The mechanism for dispensing the liquid in the dropwise fashion through the nozzle 26 from the flexible container or pouch 20 is not shown and is not part of the present invention.

The use of a flexible container, or pouch, for dispensing a liquid which is surrounded and generally supported by a rigid container is generally well known in the art. However, it is also well known in the art that problems arise in the sealing of such a flexible pouch within the rigid container to not only prevent the escape of liquid therein, but to provide an airtight seal in order that the liquid to be dispensed from the pouch is not exposed to any environment which may cause the liquid to become non sterile. These devices as can be surmised are typically used for the dispensing of preservative free liquids such as, for example, ophthalmic medications.

The cap, which may be formed from the same material as the rigid container 12, provides a means for covering the rigid container 12 and the flexible container 20 as herein and after described in greater detail.

Figure 3:
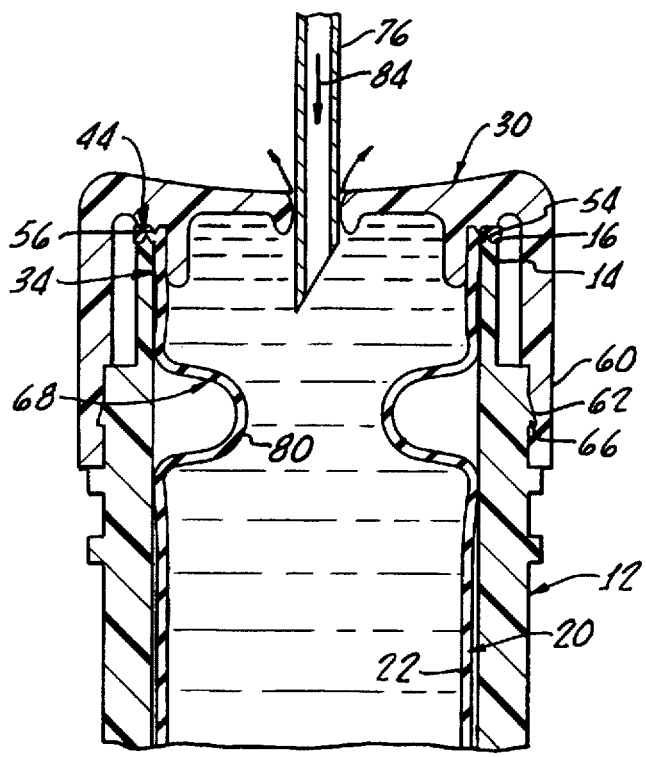
FIG. 3 is a cross sectional view similar to FIG. 2 showing the cap in position and engaging the rigid container with primary and secondary seals established along with a needle puncturing the cap which may be used for filling of the flexible container/pouch after assembling.

A plug seal indicated at 34 provides means for providing a primary seal between the rigid container 14 and the flexible pouch 20 when the cap 30 is in a position covering the rigid container 12 and the flexible pouch 20 as shown in FIG. 3. The plug seal 34 comprises, in combination, a peripheral outwardly extending wall 36 from the flexible pouch 20 and the depending portion 38 extending from the cap 30 in a downward fashion, the depending portion 38 providing a means for pressing the extending wall 36 against an inside wall 40 of the rigid container 12.

In addition, the gasket seal indicated at 44 at FIG. 3 provides a secondary seal between the rigid container 12 and the flexible container, or pouch 20. Gasket seal 44 includes, in combination, an outwardly extending lip 46 from an open end 48 of the flexible pouch 20 and a groove 50 disposed in the cap 30 for pressing the lip 48 against the top edge 16 of the rigid container open end 14.

Figure 2:
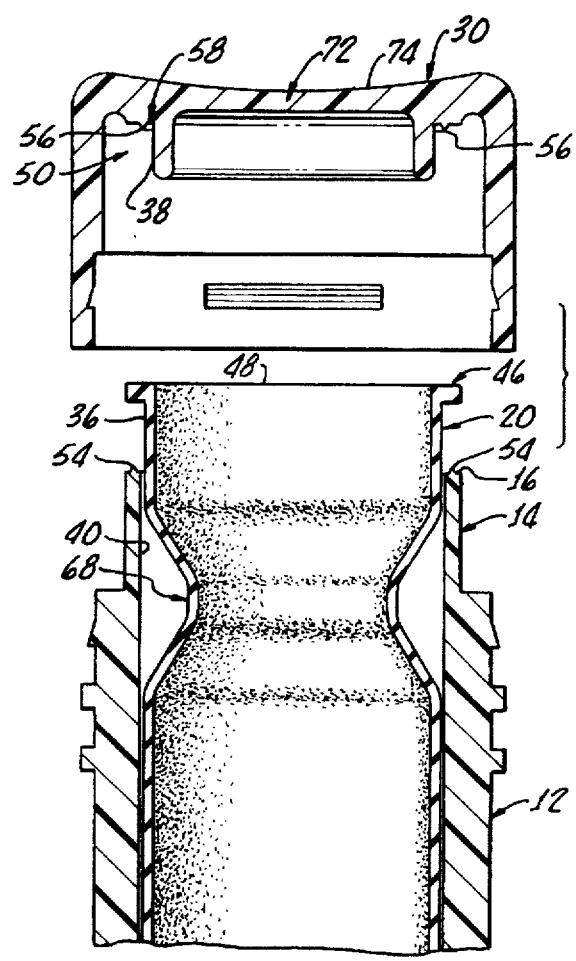
FIG. 2 is a cross sectional view taken of the top portion of the container shown at FIG. 1 along with the cap displaced therefrom before sealing of the flexible container or pouch within the rigid container.

Importantly, pointed raised ridges 54, 56 disposed or formed on the rigid container top edge 16 and a bottom 58 of the groove 50, in combination, provide rib means for preventing slippage of the lip 46 from the groove 50 particularly during assembly of the container closure apparatus 10 in which the cap 30 is moved from a spaced apart position as shown in FIG. 2 to a closed position shown in FIG. 3 in which the cap 30 is secured to the ridge container 12.

Means for securing the cap 30 to the rigid container 12 include a skirt portion 60 which is sized for placement over the rigid container 12 and includes recess portion 62 which engage protruding latch members 66 which provides a means for securing the cap 30 to the rigid container and enabling the depending portion 38 to press the extending wall 36 against the rigid container inside wall 40 as well as enabling the groove bottom 58 to press the lip 46 against the rigid container top edge 16.

As shown in FIGS. 1–4, the flexible container or pouch 20 has a length greater than a length of the rigid container 12 and a narrow region 68 in the pouch wall 20 provides a means for enabling controlled inward folding of the flexible container wall 20 when the cap 30 is secured to the rigid container 12 as shown in FIG. 3.

The lip 46 is congruent with the extending wall 34 and proximate the narrow wall portion 68.

In connection with filling the flexible container or pouch with a fluid after securing the cap 30 onto the rigid container 20 for covering the open end 14 of the rigid container 10 and the open end 48 of the flexible pouch 20, a thin portion 72 formed in the top 74 of the cap 30 provides a means not only facilitating the puncture thereof by a filling needle 76 as shown in FIG. 3, but also providing a target on the cap 30 for enabling the penetration of the needle 76 therethrough and into the flexible container 20 without touching or rupture of folds 80 in the side wall 22 produced when the cap 30 is secured to the rigid container 20.

Figure 4:
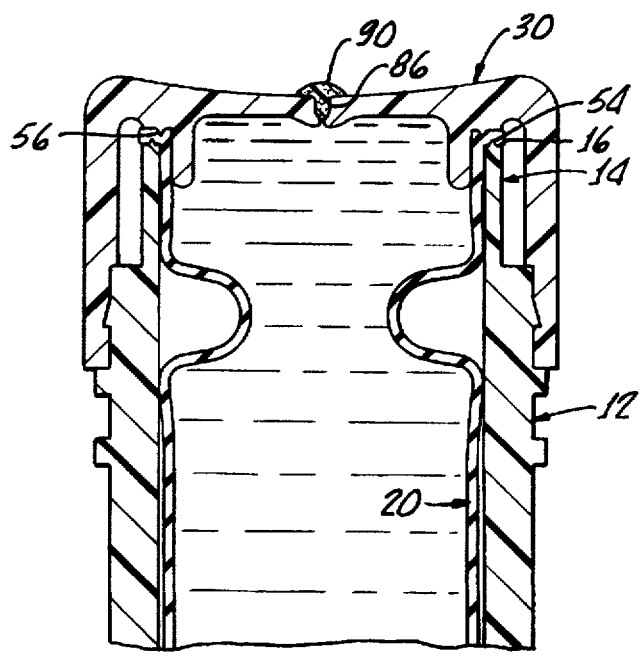
FIG. 4 is a cross sectional view similar to FIG. 3 showing the assembled container closure apparatus along with a UV cured adhesive seal filling a puncture hole in the cap made by the needle shown in FIG. 3.

After filling of the flexible pouch 20 through the needle 76 as indicated by the arrow 84, a hole 86 in the cap 30 caused by the puncturing needle 76, as shown in FIG. 4, is filled in by any conventional manner such as with a UV cured, medical grade, adhesive seal, or the like, which produces a filling material 90.

Although there has been hereinabove described a specific arrangement of a container closure apparatus in accordance with the present invention, for the purpose of illustrating the manner in which the invention may be used to its advantage, it should be appreciated that the invention is not limited thereto. Accordingly, any and all modifications, variations or equivalent arrangements which may occur to those skilled in the art, should be considered to be within the scope of the present invention as defined in the dependent claims.

What is claimed is:

1. Container closure apparatus comprising:

a rigid container having an open end with a top edge;

a collapsible container disposed within said rigid container and having an open end, said collapsible container having a length greater than a length of said rigid container and including means, defining a narrow region in said collapsible container for enabling inward folding of a collapsible container wall and containment of said collapsible container within said rigid container;

cap means for covering the rigid and collapsible container open ends;

plug seal means for providing a primary seal between said rigid container and said collapsible container, said plug seal means comprising, in combination, a peripheral outwardly extending wall portion on said collapsible container and depending portion means, extending from said cap means, for pressing the wall portion against an inside wall of said rigid container;

gasket seal means for providing a secondary seal between said rigid container and said collapsible container, said gasket seal means comprising, in combination, a lip outwardly extending from said collapsible container open end and groove means, disposed in said cap means, for pressing said lip against the rigid container top edge;

means for securing said cap means to said rigid container in a position enabling the depending portion means to press the extending wall against the rigid container inside wall and enabling the groove means to press said lip against the rigid container top edge; and rib means for preventing slippage of the lip from the groove means.

2. The container closure apparatus according to claim 1 wherein said extending wall portion is congruent with said lip.

3. The container closure apparatus according to claim 2 wherein said narrow region is disposed at a spaced apart distance from said lip.

4. The container closure apparatus according to claim 3 wherein said rib means comprises a pointed raised ridge disposed on a bottom of said groove means.

5. The container closure apparatus according to claim 4 wherein said rib means further comprises a pointed raised ridge disposed in the rigid container lip edge.

6. The container closure apparatus according to claim 5 wherein the pointed ridges on the bottom of said groove means and on the lip of the rigid container top edge are aligned with one another.

7. The container closure apparatus according to claim 1 wherein said means for securing said cap means to said rigid container comprises a skirt, sized for placement over the rigid container open end, having means for engaging said rigid container.

8. The container closure apparatus according to claim 7 wherein said rigid container includes protruding latch members and said means for engaging said rigid container includes recessed portions positioned to engage said latch members.

9. The container closure apparatus according to claim 8 wherein said cap means includes means, defining an indicated thin portion of said cap means, for facilitating needle puncture in order to fill said collapsible container with the liquid without puncture of the folded flexible container wall.

10. Container closure apparatus comprising:

a rigid container having an open end with a top edge;

flexible pouch means, disposed within said rigid container, for containing a liquid, said flexible pouch means having a collapsible side wall and an open end, said flexible pouch means having a length greater than said rigid container and including means, defining a narrow region in said collapsible side wall, for enabling inward folding of said collapsible side wall and containment of said flexible pouch means within said rigid container;

cap means for covering the rigid container and flexible pouch means open ends;

plug seal means for providing a primary seal between said rigid container and said flexible pouch means, said plug seal means comprising, in combination, a peripheral outwardly extending wall on said flexible pouch means and depending portion means, extending from said cap means, for pressing the extending wall against an inside wall of said rigid container;

gasket seal means for providing a secondary seal between said rigid container and said flexible pouch means, said gasket seal means comprising, in combination, a lip outwardly extending from said flexible pouch means open end and groove means, disposed in said cap means, for pressing said lip against the rigid container tip edge;

means for securing said cap means to said rigid container in a position enabling the depending portion means to press the extending wall against the rigid container inside wall and enabling the groove means to press said lip against the rigid container top edge; and rib means for maintaining the plug seal means and gasket seal means.

11. The container closure apparatus according to claim 10 wherein said extending wall portion is congruent with said lip.

12. The container closure apparatus according to claim 11 wherein said narrow region is disposed at a spaced apart distance from said lip.

13. The container closure apparatus according to claim 10 wherein said means for recurring said cap means to said rigid container comprises a skirt, sized for placement over the rigid container open end, having means for engaging said rigid container.

14. The container closure apparatus according to claim 13 wherein said rigid container includes protruding latch members and said means for engaging said rigid container includes recessed portions positioned to engage said latch members.

15. The container closure apparatus according to claim 14 wherein said rib means comprises a pointed raised edge disposed on a bottom of said groove means.

16. The container closure apparatus according to claim 15 wherein said rib means further comprises a pointed raised edge disposed on the rigid container top edge and the top edge pointed ridge and the groove means pointed ridge are aligned with one another.

17. The container closure apparatus according to claim 16 wherein said cap means includes means, defining an indicated thin portion of said cap means, for facilitating needle puncture in order to fill said flexible pouch with the liquid without puncture of the folded flexible pouch wall.

* * * * *